| United States Patent [19] | [11] Patent Number: 4,780,280 |
| Berger et al. | [45] Date of Patent: Oct. 25, 1988 |

[54] TEST CARRIER

[75] Inventors: Dieter Berger; Elke Biegel, both of Mannheim; Günter Frey, Ellerstadt; Hans-Rüdiger Murawski, Lampertheim, all of Fed. Rep. of Germany

[73] Assignee: Boehringer Mannheim GmbH, Mannheim, Fed. Rep. of Germany

[21] Appl. No.: 879,378

[22] Filed: Jun. 27, 1986

[30] Foreign Application Priority Data

Jun. 29, 1985 [DE] Fed. Rep. of Germany ....... 3523439

[51] Int. Cl.⁴ ............................................. G01N 31/22
[52] U.S. Cl. ......................................... 422/56; 422/58
[58] Field of Search ...................................... 422/55-58

[56] References Cited

U.S. PATENT DOCUMENTS

| 3,094,373 | 6/1963 | Luechauer | 422/61 X |
| 3,802,842 | 4/1974 | Lange et al. | 422/57 X |
| 4,046,514 | 9/1977 | Johnston et al. | 436/128 X |

*Primary Examiner*—Barry S. Richman
*Assistant Examiner*—Jill Johnston
*Attorney, Agent, or Firm*—Felfe & Lynch

[57] ABSTRACT

A test support for support-bound tests for the determination of components of fluids, especially of human and animal body fluids. The test support is composed of a plurality of layers, and the joining of the layers is accomplished at least partially by sewing.

11 Claims, 1 Drawing Sheet

TEST CARRIER

BACKGROUND OF THE INVENTION

The invention relates to a test support of a kind that is widely used especially for the determination of components of body fluids of human beings and animals.

Whereas formerly, in the clinical laboratory, the concentrations of the components of blood, for example, have been determined almost exclusively by means of liquid reagents, in recent times so-called support-bound tests have been gaining in importance. In these the reagents are embedded in appropriate layers of a solid test carrier, onto which a drop of blood, for example, is placed. The components it contains lead to a characteristic color change in the reagents on the test carrier. This color change is immediately evaluated visually, or it is measured with the aid of an instrument, usually by reflective photometry.

Such test carriers are often in the form of test strips which consist substantially of an elongated support of plastic material with test fields provided on it. However, test carriers are also known which are in the form of square or rectangular plates. The test carriers often consist of several layers which are bonded together in various ways. The bond is often produced by glues or hot-melt adhesives. In other known test carriers a plurality of layers similar to the layers of a photographic film are applied directly one on the other. Although these methods of bonding are satisfactory for a variety of purposes, in other respects they leave much to be desired. Especially when several layers cannot be glued or bonded over their entire area, for example for reasons relating to production or design, a liquid may, under certain circumstances, fail to pass rapidly and completely enough from one layer into another.

The passage of a liquid into the individual layers is improved in such a case through a proposal disclosed in U.S. Pat. No. 3,802,842 and corresponding German Pat. No. 21 18 455, in which the actual reactive coatings lie just loosely on the support and are fixed thereon by a mesh that is stretched over them andis bonded at its margins to the support. Here again, however, the transfer of liquid from layer to layer is not entirely satisfactory.

It is therefore the object of the present invention to make available a novel bonding of the layers of diagnostic test carriers, which will avoid the above-described problems and which especially will lastingly promote the transfer of liquids from layer to layer.

SUMMARY OF THE INVENTION

This object is achieved by the invention specified in the claims.

In analyses performed by support-bound tests, usually only a very small amount of liquid is available. This is especially true when a drop of blood obtained by piercing the finger or earlobe of the patient is to suffice for the analysis. Precisely in such a case a very rapid and complete transfer of the liquid between the layers of the test support is very important.

In the production of diagnostic test carriers generally, and especially in the manufacture of test strips, exacting requirements must be met. In particular, these carriers are mass-produced products which have to be manufactured in very great numbers. Surprisingly it has been found that sewing can be included in this manufacturing process without special problems. The bonds thus produced between the individual layers are reliable and lasting. Liquids can penetrate into the interstice between the sewn layers and can thus easily wet the layers. Above all, however, sewing, as it has been found in conjunction with this invention, promotes to an amazing extent the transfer of liquid between the layers bonded by sewing. At the same time monofilament sewing threads have proven to be superior sewing materials to multi-filament threads, and less absorbent synthetic materials have proven superior to the usually more absorbent natural materials (such as cotton). The liquid transfer promoting action of the threads is thus evidently not to be attributed to their absorptivity (wicking action).

The layers to be joined together do not need to be of equal size. Often layers of small area are joined to larger ones; for example, small test fields are stitched onto a larger one under it, and it has proven to be advantageous for the seams to be between 0.5 and 3 mm, preferably between 1 and 2 mm, from the nearest margin of a layer. The density of the stitches should be such that they are from 0.2 to 3 mm apart, preferably 0.5 to 2 mm apart, based on a simple, straight seam. Zig-zag stitching is also possible, but less preferred because it requires more space. If the stitches are too far apart, the transfer of liquid between the sewn layers will not be sufficient. If the stitches are too close together, there will be an excessive resistance to flow transversely of the seam. Moreover, the holes produced by the sewing needles absorb too large a portion of the liquid that is to be analyzed.

A plurality of seams can be used. A system has proven especially suitable in which at least two seams are disposed approximately parallel to one another at a distance of no more than 15 mm, preferably no more than 10 mm apart. The two seams serve first to keep the layers substantially flat against one another. Secondly, the liquid rapidly passes from one layer into the other at the seams and then diffuses uniformly from the two seams in the layer that is to be wetted. The above-mentioned measures regarding the arrangement of the seams combined to produce an optimum bonding as regards reliability and rapid transfer of liquid between the layers.

Special problems exist in test carriers, especially test strips, which have a base made of a stiff plastic film. The plastic films in this case must be stiff enough to be handled easily. In order to permit the use of the new sewing technique in such test supports, in a preferred embodiment of the invention a sandwich construction with at least three layers is proposed, in which the reaction layer is not stitched directly to the support, but is sewed with a connecting layer interposed. Then the connecting layer is bonded to the support with a hot-melt adhesive. The connecting layer in this case consists of a material which on the one hand is soft enough to be pierced easily by the sewing needles, and on the other hand is strong enough to resist tearing by the sewing threads. Moreover it must be able to be well bonded to the base film. For example, a plastic material that is sold under the trademark name Depron by Kalle of Wiesbaden, Federal Republic of Germany, has proven useful. Additional developments and advantages of the present invention will be explained in the following description of an embodiment, with the end of the drawings.

DESCRIPTION OF THE PREFERRED EMBODIMENT

Figure 1:
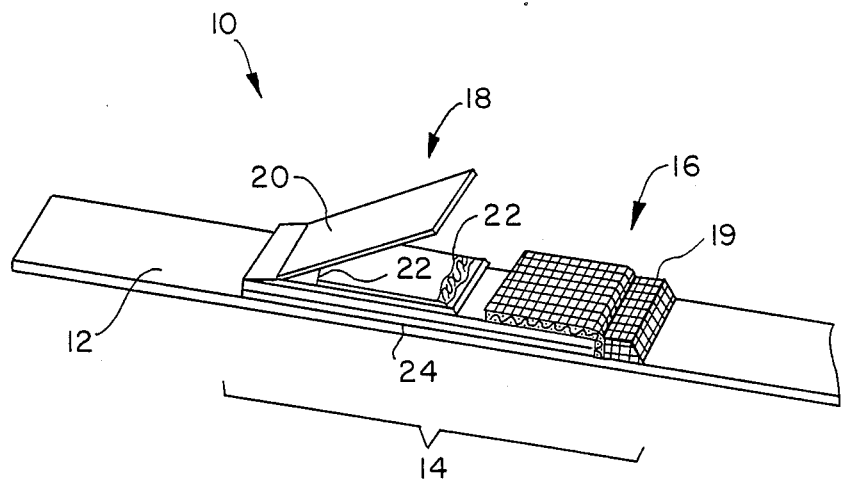
FIG. 1 is a simplified perspective representation of a test carrier according to the invention.

The test carrier 10 represented in FIG. 1 is in the basic form of a conventional test strip. It is, however, a high-quality analytic tool that is hardly comparable with the former test strip. On a base 12 of plastic film there is disposed a test area which is generally identified by the number 14. In the present case the support is one which permits analyses directly from whole blood instead of plasma. Glass fibers are used for the separation of the erythrocytes. Further details are to be found in the European patent application with the publication number 45 476 and in the corresponding U.S. Pat. No. 4,477,575.

The test area 14 of the test support 10 can be divided into an application zone 16 and an analysis zone 18. The application zone 16 is covered by a protective mesh 19. In the analysis zone can be seen a flap 20. The layers under the flap are sewed together with seams 22.

The sandwich construction of the test carrier is identified as a whole by the number 24. Details are to be found in the following description of FIG. 2.

Figure 2:
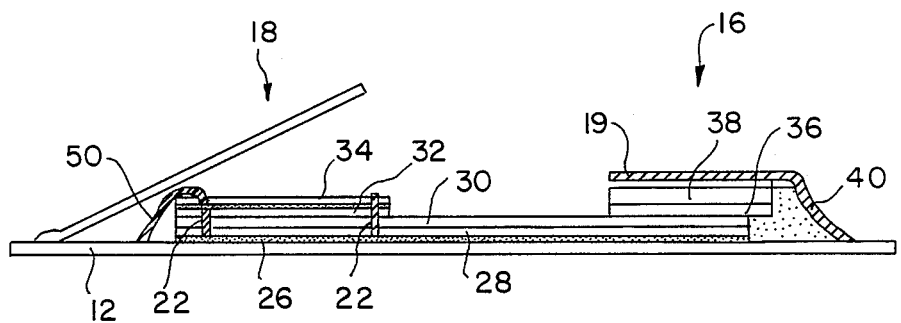
FIG. 2 is a side view of the sandwich construction of a preferred embodiment of the invention.

FIG. 2 shows a side view of the construction of the test area 14 of a preferred embodiment of a test carrier 10 according to the invention, which is suitable for the determination of creatinine. Such a test involves special requirements in regard to the construction of a test support, which are satisfied according to the invention. The invention, however, is also suitable for other determinations.

The support base 12 consists, as mentioned, of a plastic film such as is commonly used in the production of test strips. This film must be sufficiently stiff for the handling and production of the test supports. It has been found in connection with the invention that such a plastic film can be sewn directly only with great difficulty.

By means of a hot-melt adhesive 26, a multi-layer sandwich is bonded to the support base, the sandwich consisting of a connecting layer 28, a liquid transfer layer 30, a reactive layer 32, and a hold-down layer 34. These four layers are fastened together by stitched seams 22. After sewing they are glued as a whole onto the support base 12.

Whereas the reactive layer 32 and the hold-down layer 34 lie only in the area of the analysis zone 18, the connecting layer 28 and the liquid transfer layer 30 extend all the way into the application zone 16. Above them in this zone are a preliminary reaction layer 36, a plasma gathering layer 38, and the protective mesh 19, which are cemented along one side by a strip of hot-melt adhesive 40.

Details of the sewing technique according to the invention will first be explained. Then special facts concerning the creatinine test will be described, which is the test described in the preferred embodiment.

As stated above, the sewing together of test carrier layers has the the advantage especially that a reliable transfer of liquid is assured between the layers of the test support in the direction perpendicular to their surface, even when the amounts of the liquid are very small. In the embodiment represented, the liquid is blood plasma, which is produced in a small amount of, for example, about 20 microliters, in the application zone. For this purpose a drop of blood is placed on the protective mesh 19, penetrates through the plasma gathering layer 38 in which the erythrocytes are separated, and the plasma passes through the preliminary reaction layer 36 into the liquid transport layer 30. In the latter it is transported by capillary action leftward in the drawing, into the analysis zone 18. Details are to be found in the cited European patent application No. 45,476. (corresponding to U.S. Pat. No. 4,477,575).

The liquid transport layer 30 consists preferably of a very fine and therefore mechanically delicate material with many thin fibers with voids between them to assure a good capillary action. The liquid is to pass very quickly and substantially from the liquid transport layer into the reaction layer 32. This transfer of the liquid is promoted according to the invention by the fact that the two layers are sewn together by the seams 22.

The sewing technique is generally advantageous even when only two layers of a test support are sewn together. The use of the additional bond layer is especially preferred, however, when the support base 12 is a plastic film that is so stiff that it is difficult to sew. In this case the connecting layer is sewn to the reaction layer and the sandwich thus formed is glued to the support base. In this case it is preferred, but not necessary, to place the liquid transport layer 30 as a separate layer between the connecting layer 28 and the reaction layer 32. Instead of this, the bond layer itself could also be made as a liquid transport layer. A plastic film would be suitable that is sufficiently strong for sewing and has a capillary surface structure at least on the upper surface in the figure so as to serve simultaneously as a liquid transport layer. Also suitable would be a spreading layer, as described in German Pat. No. 23 32 760 and in the corresponding U.S. Pat. No. 3,992,158. In this case, therefore, the built-up sandwich would consist of at least three layers, namely the support layer, the connecting layer and the reaction layer, the reaction layer and connecting layer being sewn together and placed together on the support layer.

The reaction layer can be, for example, a film containing the reagents or a paper or nonwoven material impregnated with the reagents. Especially in cases in which the reaction layer is made of a material that swells up in the moist state, it may be desirable to sew on an additional hold-down layer 34. This can be in the form, for example, of a porous mesh which consists of a nonabsorbent material that is dimensionally stable in liquid, especially a plastic material. Such a hold-down layer 34 is provided in FIG. 2 in addition to a sandwich already composed of four layers. Even in the case of any other set of layers, however, it can also be a valuable addition to the sewing technology according to the invention. If the hold-down layer consists of an impregnable material, it can be impregnated with reagents.

In the especially preferred case in which the test support structure according to the invention is used for the determination of creatinine, the following applies:

The determination of creatinine is performed according to the following known reaction:

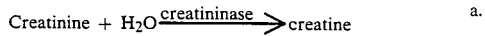

a.

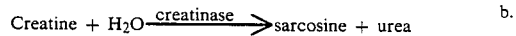

b.

-continued

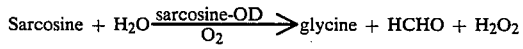

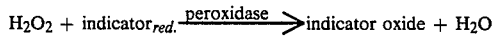

The reaction step d is preferably the indicator reaction described in German patent application No. 34 33 946, corresponding to U.S. patent application Ser. No. 774,353, and in this case all reagents except the aniline phosphonic acid used as coupler for the indicator are contained in the form of a reagent film in the flap 20.

Underneath the plasma gathering layer 38, which consists of nonwoven glass fiber material which satisfies the specifications of the cited European patent application No. 45 476, (U.S. Pat. No. 4,477,575) the preliminary reaction layer 36 is a creatine separating paper which contains all the reagents for the separation of endogenic creatine, i.e., the creatine present in the sample. This is necessary because the reaction for the detection of creatinine uses creatine as an intermediate and therefore endogenic creatine would falsify the test.

The liquid transport layer 30 is in the form of glass fiber cloth or nonwoven glass fiber material of low strength and good liquid transfer properties. In addition to transporting the plasma, the glass fibers serve the purpose of holding back any erythrocytes that may not have been completely removed in the plasma gathering layer 38 as the plasma passes from the application zone 16 to the analysis zone 18.

The reaction layer 32 in this test is also used as a preliminary reaction layer and contains the same reagents as layer 36. The hold-down layer 34 simultaneously serves as a component for the component aniline phosphonic acid not contained in the flap 20, as mentioned above.

A creatinine determination with a testing system of this kind is performed as follows:

30 microliters of blood is measured onto the protective mesh 19. The blood penetrates into the plasma recovery layer 38 where the erythrocytes are separated from the plasma. Then the plasma penetrated into the creatine separating paper 36, where the following reaction takes place:

 (a)

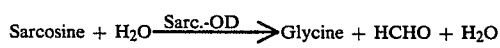 (b)

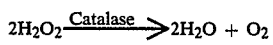 (c)

It is important to prevent the catalase from being taken into the rest of the test, since it would interfere with the detection reaction. It is therefore fixed on the creatine separating paper support.

The plasma preincubated with the creatine separating reagents flows by capillary action through the liquid transport layer into the analysis zone 18. Through the two seams the second creatine separating paper used as reaction layer 32 is wetted with plasma. The two plasma fronts that then develop run toward one another from the two seams and completely fill the creatine separating paper 32. On account of the great consequences of interference by creatine, it is especially important in a test of this kind that the reaction layer 32 used for the creatine separation be wetted rapidly and completely. Here the stitching has proven to be especially helpful. The liquid further penetrates also to the hold-down layer 34, dissolving the aniline phosphonic acid contained therein. Moreover the hold-down layer 34 presses against the creatine separating paper 32 beneath it and helps to wet it completely.

In this stage the test requires a relatively long preincubation time of, in this case, about 100 seconds, which is necessary for the separation of the endogenic creatine. Not until then can the flap of reaction film 20 be pressed down. To prevent premature contact between the flap of reaction film 20 and the hold-down layer 34 with the reaction solution contained therein, a protective film 50 is provided, which is stitched on one side to the sandwich 24 by means of one of the seams 22 along a line running transversely across the test strip.

At the end of the preincubation period for the removal of the endogenic creatine, the flap of reaction film is pressed against the hold-down layer in a complete and bubble-free manner, preferably by a suitable mechanism in an evaluating apparatus. The color change takes place and is evaluated by reflection photometry.

We claim:

1. A clinical analysis test carrier for determining the concentration of a componenet of a body fluid of human beings and animals comprising a base layer of a stiff plastic film at last one reaction layer including reagent means for reacting with the component to form a color change characteristic of said component, and a connecting layer disposed between the base layer and the at least one reaction layer, the connecting layer being sewn to the reaction layer with stitches and the base layer being joined to the connecting layer by means other than stitches.

2. The test carrier according to claim 1, wherein stitches are monofil threads.

3. The test carrier according to claim 1, where said layers are joine by at least two seams formed from said stitches and wherein said seams are no more than 10 mm apart.

4. The test carrier according to claim 1, further comprising an additional hold-down layer disposed on one of said layers.

5. The test carrier according to claim 1, wherein the connecting layer, is a liquid transport layer.

6. The test carrier according to claim 1, further comprising a liquid transport layer disposed between the connecting layer and the reaction layer.

7. The test carrier of claim 1 wherein said base layer and said connecting layer are joined by gluing.

8. The test carrier according to claim 1 in herein said stitches are spaced 0.2 to 3 mm apart.

9. The test carrier according to claim 8, wherein said stitches are sapced from 0.5 to 2 mm apart.

10. The test carrier according to claim 1, wherein said stitches are at a distance from a margin of the joined layers of 0.5 to 3 mm.

11. The test carrier according to claim 10, wherein said stitches are at a distance from said margin of from 1 to 2 mm.

* * * * *

UNITED STATES PATENT AND TRADEMARK OFFICE
CERTIFICATE OF CORRECTION

PATENT NO. : 4,780,280
DATED : October 25, 1988
INVENTOR(S) : Dieter Berger, et al.

It is certified that error appears in the above-identified patent and that said Letters Patent is hereby corrected as shown below:

Column 2, last line: change "end" to -- aid --.

Column 6, line 30: change "componenet" to -- component --;
         line 32: change "last" to -- least --;
         line 41: before "stitches" insert -- said --;
         line 43: change "joine" to -- joined --;
         line 57: change "in herein" to -- wherein --;
         line 59: change "sapced" to -- spaced --.

Signed and Sealed this

Ninth Day of May, 1989

*Attest:*

DONALD J. QUIGG

*Attesting Officer*       *Commissioner of Patents and Trademarks*